US005701899A

United States Patent [19]

Porter

[11] Patent Number: 5,701,899
[45] Date of Patent: *Dec. 30, 1997

[54] PERFLUOROBUTANE ULTRASOUND CONTRAST AGENT AND METHODS FOR ITS MANUFACTURE AND USE

[75] Inventor: Thomas R. Porter, Omaha, Nebr.

[73] Assignee: The Board of Regents of the University of Nebraska, Lincoln, Nebr.

[*] Notice: The term of this patent shall not extend beyond the expiration date of Pat. No. 5,560,364.

[21] Appl. No.: 454,853

[22] Filed: May 31, 1995

Related U.S. Application Data

[63] Continuation-in-part of Ser. No. 252,286, Jun. 1, 1994, Pat. No. 5,567,415, which is a continuation-in-part of Ser. No. 301,146, Sep. 6, 1993, Pat. No. 5,578,291, which is a continuation of Ser. No. 113,415, Aug. 27, 1993, abandoned, which is a continuation-in-part of Ser. No. 60,751, May 12, 1993, abandoned, which is a continuation-in-part of Ser. No. 57,298, May 4, 1993, abandoned.

[51] Int. Cl.$^6$ .................. A61B 8/00; A61K 49/00
[52] U.S. Cl. .................. 428/662.02; 424/9.52
[58] Field of Search .................. 424/450, 9.52; 128/662.02

[56] References Cited

U.S. PATENT DOCUMENTS

| | | |
|---|---|---|
| 4,572,203 | 2/1986 | Feinstein . |
| 4,634,586 | 1/1987 | Goodwin et al. .......... 424/1.1 |
| 4,718,433 | 1/1988 | Feinstein . |
| 4,774,958 | 10/1988 | Feinstein . |
| 4,844,882 | 7/1989 | Widder et al. . |
| 4,957,656 | 9/1990 | Cerny et al. . |
| 5,040,537 | 8/1991 | Katakura . |
| 5,107,842 | 4/1992 | Levene et al. . |
| 5,255,683 | 10/1993 | Monaghan . |
| 5,304,325 | 4/1994 | Kaufman et al. .......... 252/312 |
| 5,310,540 | 5/1994 | Giddey et al. . |
| 5,315,997 | 5/1994 | Widder et al. . |
| 5,315,998 | 5/1994 | Tachibana et al. . |
| 5,380,519 | 1/1995 | Schneider et al. . |
| 5,385,147 | 1/1995 | Anderson et al. . |
| 5,385,725 | 1/1995 | Lin et al. . |
| 5,393,524 | 2/1995 | Quay . |
| 5,401,493 | 3/1995 | Lohrmann et al. . |
| 5,409,688 | 4/1995 | Quay . |
| 5,410,516 | 4/1995 | Uhlendorf et al. . |
| 5,413,774 | 5/1995 | Schneider et al. . |
| 5,439,686 | 8/1995 | Desai et al. . |
| 5,445,813 | 8/1995 | Schneider et al. . |
| 5,540,909 | 7/1996 | Schutt .................. 424/9.52 |
| 5,542,935 | 8/1996 | Unger et al. .......... 604/190 |
| 5,552,133 | 9/1996 | Lambert et al. ........ 424/9.52 |
| 5,558,853 | 9/1996 | Quay .................. 424/9.5 |
| 5,560,364 | 10/1996 | Porter .................. 128/662.028 |
| 5,567,415 | 10/1996 | Porter .................. 424/9.52 |

FOREIGN PATENT DOCUMENTS

| | | | |
|---|---|---|---|
| 0 633 030 A1 | 1/1995 | European Pat. Off. ........ | A61K 49/00 |
| WO 92/05806 | 4/1992 | WIPO .................. | A61K 49/00 |
| WO 93/05819 | 4/1993 | WIPO .................. | A61K 49/00 |
| WO 95/23615 | 9/1995 | WIPO .................. | A61K 49/00 |

OTHER PUBLICATIONS

Porter, "The Mechanism and Clinical Implication of Improved Left Ventricular Videointensity Following Intravenous Injection of Multi-Fold Dilutions of Albumin With Dextrose", *Int. J. Card Imaging*, Jun. 1995, vol. 11, No. 2, pp. 117–25, XP000590839.

Xie F. et al., "Acute Myocardial Ischemia and Reperfusion Can be Visually Identified Non-Invasively with Intraveneous Perfluoropropane-Enhanced Sonicated Dextrose Albumin Ultrasound Contrast", Abstract No. 2989, 67th Scientific Sessions of the American Heart Assoc., Dallas, TX, USA, Nov. 14–17, 1994. Circulation, 1994, vol. 90, No. 4 part 2, p. 1555, XP000577054.

Porter, et al., "Echocardiographic Detection of Residual Coronary Flow Abnormalities and Stenosis Severity After Coronary Reperfusion Using Intravenous Perfluoropropane-Enhanced Sonicated Dextrose Albumin", Abstract No. 955–60, 44th Annual Scientific Session of the American College of Cardiology, New Orleans, LA, USA, Mar. 19–22, 1995. In: *Journal of the American College of Cardiology*, Spec. Issue, p. 205A., XP000577058.

Putterman, S., "Sonoluminescence: Sound into Light", Feb. 1995, *Scientific American*, 46–51.

Evans, W., 1992, Chapter 5, "Influence of Protein Binding", 3rd Ed., *Applied Pharmacokinetics: Principles of Therapeutic Drug Monitoring*.

Kumar, S., 1995, "Characterization of Binding Sites, Extent of Binding, and Drug Interactions of Oligonucleotides with Albumin", *Antisense Research and Development*, 5:131–139, Mary Ann Liebert, Inc.

Kricsfeld et al, "Detection of Regional Perfusion Abnormalities During Adenosine Stress Echocardiography Using Intraveneous Perfluoropropane-Enhanced Sonicated Dextrose Albumin", Abstract No. 703–2, 44th Annual Scientific Session of the American College of Cardiology, New Orleans, LA, USA, Mar. 19–22, 1995. In: *Journal of the American College of Cardiology*, Spec. Issue, p. 38A, XP000577057.

(List continued on next page.)

*Primary Examiner*—Francis Jaworski
*Attorney, Agent, or Firm*—Zarley, McKee, Thomte, Voorhees & Sease

[57] ABSTRACT

The invention relates to a new ultrasound contrast agent of the type which relies on microbubbles for echogenicity. The new contrast agent comprises microbubbles with an internal atmosphere enhanced with a perfluorobutane gas which is effective for visually detecting myocardial uptake upon echocardiogram following peripheral intravenous injection of said agent into a host. The contrast agent of this invention is unique in that it makes possible the non-invasive visual detection of myocardial uptake. In addition, the contrast agent of this invention makes feasible safe and consistent, non-invasive methods for visually assessing, qualitatively or quantitatively, not only myocardial perfusion, but renal and hepatic perfusion, and for detecting severity of coronary arterial stenosis.

15 Claims, No Drawings

OTHER PUBLICATIONS

Porter, et al, "Multifold Sonicated Dilutions of Albumin with Fifty Percent Dextrose Improve Left Ventricular Contrast Videointensity After Intravenous Injection in Human Beings", abstract, *J. Am. Soc. Echocardiogr.*, Sep.–Oct. 1994, vol. 7, No. 5, pp. 465–71, XP000590864.

Xie, et al, "Perfluoropropane Enhanced Sonicated Dextrose Albumin Produces Visually Apparent Consistent Myocardial Opacification With Physiologic Washout and Minimal Hemodynamic Changes Following Venous Injection", Apstract No. 362, 67th Scientific Sessions of the American Heart Association, Dallas, TX, USA, Nov. 14–17, 1994, In: Circulation, 1994, vol. 90, No. 4, Part 2, p. 269,, XP000577055.

Porter, et al, "Visually Discernible Myocardial Echocardiographic Contrast After Intravenous Injection of Sonicated Dextrose Albumin Microbubbles Containing High Molecular Weight, Less Soluble Gases", abstract, *J Am Coll Cardiol*, Feb. 1995, vol., 25, No. 2, pp. 509–15, XP000590866.

Porter, et al, Noninvasive Identification of Acute Myocardial Ischemia and Reperfusion With Contrast Ultrasound Using Intravenous Perfluoropropane–Exposed Sonicated Dextrose Albumin, abstract, *J Am Coll Cardiol*, Jul. 1995, vol. 26, No. 1, pp. 33–40, XP000590865.

1

PERFLUOROBUTANE ULTRASOUND CONTRAST AGENT AND METHODS FOR ITS MANUFACTURE AND USE

CROSS-REFERENCE TO A RELATED APPLICATION

This application is a continuation-in-part application of U.S. patent application Ser. No. 08/252,286 filed by Thomas R. Porter on Jun. 1, 1994 and now U.S. Pat. No. 5,567,415, which is a continuation-in-part application of U.S. Ser. No. 08/301,146 filed by Thomas R. Porter on Sep. 6, 1993 and now U.S. Pat. No. 5,578,291, which is a continuation of U.S. patent application Ser. No. 08/113,415 filed by Thomas R. Porter in Aug. 27, 1993 and now abandoned, which is a continuation-in-part application of U.S. application Ser. No. 08/060,751 filed by Thomas R. Porter on May 12, 1993 and now abandoned, which is a continuation-in-part application of U.S. patent application Ser. No. 08/057,298 filed by Thomas R. Porter on May 4, 1993 now abandoned. All of said applications are commonly owned.

FIELD OF THE INVENTION

This invention relates to a new and improved ultrasonic contrast agent and to its manufacture and use in ultrasonic imaging and echocardiography. More particularly, the contrast agent of this invention relates to the sonicated microbubble type, but is unique in that it makes possible the non-invasive visual detection of myocardial uptake, as discussed more fully hereinafter. In addition, the contrast agent of this invention makes feasible safe and consistent, non-invasive methods for visually assessing, qualitatively or quantitatively, not only myocardial perfusion, but renal and hepatic perfusion, and for detecting severity of coronary arterial stenosis.

BACKGROUND OF THE INVENTION

Ultrasonic imaging is used as a diagnostic tool to aid in therapeutic procedures. It is based on the principle that waves of sound energy can be focused upon an area of interest and reflected to produce an image. Generally, an ultrasonic transducer is placed on a body surface overlying the area to be imaged, and ultrasonic energy, produced by generating and receiving sound waves is transmitted. The ultrasonic energy is reflected back to the transducer where it is translated into an ultrasonic image. The amount and characteristics of the reflected energy depend upon the acoustic properties of the tissues, and contrast agents which are echogenic are preferentially used to create ultrasonic energy in an area of interest and improve the image received.

In ultrasound imaging, videotape images obtained following contrast injection are digitized, allowing the gray scale to be quantified from 1 to 225 gray scale units for 30 cardiac cycles. The contrast intensity is plotted on the vertical axis against time on the horizontal axis. The peak videointensity (corrected for baseline intensity) is determined as the highest point on the time intensity curve.

For a discussion of contrast echographic instrumentation, see, for example, De Jong N, "Acoustic properties of ultrasound contrast agents", CIP-GEGEVENS KONINKLIJKE BIBLIOTHEEK, DEN HAG (1993), pages 120 et seq.

Contrast echocardiography has been used to delineate intracardiac structures, assess valvular competence, and demonstrate intracardiac shunts. Myocardial contrast echocardiography (MCE) has been used to measure coronary blood flow reserve in humans. MCE has been found to be a safe and useful technique for evaluating relative changes in myocardial perfusion and delineating areas at risk.

A multiplicity of potential ultrasonic imaging agents has been reported for contrast echocardiography. No such agent routinely attains visually discernible myocardial uptake following peripheral intravenous injection. Although there have been many reports of transpulmonary transmission of ultrasound contrast agents following intravenous injection and despite the fact that myocardial opacification on echocardiogram can be produced by left sided injection of such contrast agents, visualization of myocardial contrast has not been achieved by intravenous administration of sonicated microbubbles.

Most recently, sonicated albumin and sonicated dextrose/albumin have been shown to produce variable degrees of left ventricular chamber ultrasound contrast following intravenous injection. (See Villanueva et al. Circulation 85:1557–1564, 1992; Lin et al. Int J Card Imaging 8:53–6, 1992; Feinstein et al. J Am Coll Cardiol 16:316–224, 1990; Keller et al. Am Heart J 114:570–575, 1987; and Shapiro et al. J Am Coll Cardiol 16:1603–1607, 1990). The microbubbles of these contrast agents are small (4–6 microns) and are capable of swift transpulmonary passage. However, visually discernible myocardial uptake of such microbubbles following peripheral intravenous injection has not been possible because of the rapid diffusion of blood soluble oxygen and nitrogen inside the microbubble into the blood which consequently loses its ultrasound reflective properties (e.g., see Porter et al. J Am Soc Echocard Supplement 7:S1, May 1994, and Weyman AE: Principles and Practice of Echocardiography, Malvern, Pa.: Lea & Febiger, 1994; pp. 302–26.)

An important objective of this invention is to provide a contrast agent and methods for its production and use wherein microbubble survival and subsequent myocardial ultrasound contrast is improved sufficiently to make possible visually discernible myocardial uptake of such microbubbles following non-invasive peripheral intravenous injection. This and other objectives of this invention will become apparent in the following discussion.

SUMMARY OF THE INVENTION

In accordance with this invention, there is provided an improved ultrasound contrast agent which relies on microbubbles for echogenicity, which comprises enhancing the internal atmosphere of the microbubbles with an amount of perfluorobutane gas which is effective for visually detecting myocardial uptake upon echocardiogram following peripheral intravenous injection of said agent into a host. The perfluorobutane gas content of the microbubbles is sufficient to lower microbubble gas solubility and diffusivity in vivo in blood. Generally, the minimum amount of perfluorobutane gas in the microbubbles which is effective is that amount which results in microbubbles which pass reliably through the pulmonary circulation without collapse. This is evidenced by opacification of the myocardium of the left ventricle of the heart following intravenous injection and can be visually discerned by echocardiography, for example, in accordance with standard methods or the methods described more fully hereinafter.

Consequently, the invention also provides a method of ultrasonic imaging for use in medical procedures, comprising the steps of injecting the unique perfluorobutane-containing microbubbles of this invention into a host to thereby alter the acoustic properties of a predetermined area, and ultrasonically scanning an area including said predetermined area so as to obtain an image of said predetermined area.

DETAILED DESCRIPTION OF THE INVENTION

The perfluorobutane-enhanced contrast agents of the invention comprise any contrast agent for ultrasonic imaging which relies on microbubbles for ecogenicity the interior of which are enhanced with perfluorobutane gas. The use of perfluoropropane gas ($C_3F_8$) to enhance the internal atmosphere of microbubble contrast agents has been described in my previously filed and pending application U.S. Ser. No. 08/057,298 filed on May 4, 1993. This invention related to the discovery that perfluorobutane gas ($C_4F_{10}$) or decafluorobutane results in much improved contrast over traditional contrast agents and even over any perfluorocarbon gas contrast agent including perfluoropropane and perfluoropentane. Perfluoropentane is plagued by side effects as it is liquid a room temperature and once injected into the higher temperature of the body it tends to expand uncontrollably which can lead to increased pulmonary pressure and toxicity after ultrasound is completed.

Perfluorobutane ($C_4F_{10}$) has been previously demonstrated as safe for intraocular injection in humans. It has also been used in human studies for intraocular injections to stabilize retinal detachments (Wong and Thompson, Ophthalmology 95:609–613) and is useful in treating complicated retinal detachments by providing internal tamponade of retinal breaks.

For most ultrasound imaging, the contrast agent is formulated in a pharmaceutically effective dosage form for peripheral administration to the host to be imaged. Generally such host is a human subject although other mammalian hosts, such as canine or equine can be imaged effectively. In a most preferred embodiment the contrast agent is a sonicated mixture of commercially available albumin (human), USP, solution (generally supplied as 5% or a 25%, by weight, sterile aqueous solutions), and commercially available dextrose, USP, for intravenous administration are employed. This mixture is sonicated under ambient conditions, i.e., room air, temperature and pressure, and is perfused with perfluorobutane during sonication.

In a preferred embodiment the invention uses a microbubble contrast agent wherein the microbubbles are stabilized by a filmogenic, de-naturable protein coating. Suitable proteins include naturally occurring proteins such as albumin, human gammaglobulin, human apotransferrin, Beta-lactose, and urease. The invention preferably employs a naturally occurring protein, but synthetic proteins may also be used. Particularly preferred is human serum albumin.

Although intravenous echo contrast agents made from sonicated microbubbles are known (e.g., ALBUNEX, Molecular Biosystems, Inc.) and can be employed in this invention, it is preferred to use a sonicated aqueous solution containing a mixture of a pharmaceutically acceptable saccharide, e.g., dextrose, and a protein, e.g., albumin. Generally, sonication is performed in an air atmosphere. In an especially preferred embodiment, dextrose, which is readily available in pharmaceutically acceptable dosage forms, is the preferred saccharide and human serum albumin is the preferred protein. The preferred embodiment would include a two-fold to eight-fold dilution of 5%–50% by weight of dextrose and a 2%–10% by weight of human serum albumin. Exemplary of other saccharide solutions of this invention are an aqueous monosaccharide solution (e.g. having the formula $C_6H_6O_{12}$, such as, the hexoses, dextrose or fructose, or mixtures thereof), aqueous disaccharide solution (e.g., having the formula $C_{12}H_{22}O_{11}$, such as sucrose, lactose or maltose, or mixture thereof), or aqueous polysaccharide solution (e.g., soluble starches having the formula $(C_6H_{10}O_5)_n$, wherein n is a whole integer between about 20 and about 200, such as amylose or dextran, or mixtures thereof. Sonication by ultrasonic energy causes cavitation within the dextrose-albumin solution at sites of particulate matter or gas in the fluid. These cavitation sites eventually resonate and produce small microbubbles (about 4 to about 7 microns in size) which are non-collapsing and stable. In general, sonication conditions which produce concentrations of greater than about $4 \times 10^8$ m of between about 5 and about 6 micron microbubbles are preferred.

The mean microbubble size of sonicated dextrose albumin ranges from between about 5 to about 6 microns. This is a good size as it has been observed that microbubble radius decreases as a function of time in a still liquid due to a diffusion gradient present between the internal and external gases of the microbubble. An increase in microbubble size has a significant effect on the persistence of a microbubble within blood. It must also be of a size sufficient for transpulmonary passage. It must have a mean diameter of less than 10 microns and greater 0.1 microns. Since the size of albumin microbubbles is ideal (between 5 and 6 microns) for transpulmonary passage, the major reason for the significant loss in left ventricular and myocardial videointensity produced following intravenous injection of albumin coated microbubbles is due to the significant diffusion of gases within the microbubble following intravenous injection during transit to the left ventricular cavity. Sonicated dextrose albumin enhanced with an inert gas such as perfluorobutane gas, having a lower blood solubility than air, produces a significantly higher left ventricular and myocardial videointensity than sonicated albumin alone.

In addition to myocardial imaging the contrast agents of this invention are useful for renal and hepatic imaging. Thus, another embodiment of this invention provides a method for myocardial, renal or hepatic opacification. The method preferred involves obtaining an echo contrast agent of this invention, introducing said echo contrast agent into a host by intravenous injection, and performing an echo contrast study on said host using a suitable Doppler or ultrasound echo apparatus as discussed more fully hereinafter.

The method of ultrasonic imaging in which microbubbles formed by sonicating an aqueous protein solution are injected into a mammal to alter the acoustic properties of a predetermined area which is then ultrasonically scanned to obtain an image of the area for use in medical procedures is well known (e.g., see U.S. Pat. No. 4,572,203, U.S. Pat. No. 4,718,433 and U.S. Pat. No. 4,774,958, the contents of each of which are incorporated herein by reference). It is the use of the unique, stabilized perfluorobutane-containing microbubbles of this invention which constitutes a novel improvement over even other perfluorocarbon gases. Thus, in accordance with another embodiment of this invention, there is provided a method of ultrasonic imaging for use in medical procedures comprising the steps of forming an aqueous protein solution (e.g., aqueous dextrose albumin), subjecting said solution to high frequency sonication while exposed to perfluorobutane gas, said sonication forming stabilized microbubbles of relatively uniform size, containing said perfluorobutane, and capable of transpulmonary passage, and using the stabilized microbubbles as an injectable contrast agent for said ultrasonic imaging.

Sonicated albumin has been used to study coronary flow reserve and immediate post-angioplasty anterograde blood flow reserve in humans. In humans without significant coronary artery disease, left main coronary artery injections of sonicated albumin before and after intracoronary papaverine result in time intensity curves which can be utilized to determine coronary flow reserve. It has been demonstrated that the washout of ultrasound contrast from the human myocardium in this setting correlates with coronary flow reserve measured by more invasive techniques.

Secondly, intracoronary sonicated albumin injections in humans with coronary artery disease, before and after angioplasty, has been done. The functional reserve of the myocardium supplied by the vessel undergoing angioplasty is immediately improved following angioplasty. The degree of improvement depends not on how visually successful the angioplasty was, but on how quantitatively successful the improvement in stenosis area was after angioplasty. Sonicated albumin does not reliably cross the pulmonary circulation into the left ventricular chamber following an intravenous injection, and thus at present cannot be used to non-invasively detect myocardial blood flow.

It has been observed that a microbubble radius decreases as a function of time in a still liquid due to a diffusion gradient present between the internal and external gases of the microbubble. An increase in microbubble size has a significant effect on the persistence of a microbubble within blood. The mean microbubble size of sonicated dextrose albumin ranges from between about 5 to about 6 microns. Since this size is ideal for transpulmonary passage, the major reason for the significant loss in left ventricular and myocardial videointensity produced following intravenous injection is due to the significant diffusion of gases within the microbubble following intravenous injection during transit to the left ventricular cavity. Sonicated dextrose albumin enhanced with an inert gas such as perfluorobutane, having a lower blood solubility than air, produces a significantly higher left ventricular and myocardial videointensity than sonicated albumin alone.

Because of high surface tension, the concentration of nitrogen and oxygen gas within the microbubble is much higher than that in blood, and thus there is a rapid diffusion of this gas into the blood stream following intravenous injection. Wible et al. (Circulation, 88:I-401, 1993) demonstrated that this diffusion process can be accelerated if one decreased the partial pressure of nitrogen within the blood stream by decreasing the inhaled fraction of nitrogen. This lower external concentration of nitrogen results in loss of the left ventricular videointensity produced by the same intravenous injection of sonicated albumin while inhaling room air. It has also been observed that oxygen rapidly diffuses out of gas bubbles into human blood (See Yang et al., J Biomech 3:275, 1971).

Both nitrogen and oxygen diffuse rapidly across these concentration gradients, but nitrogen appears to dissolve more slowly than oxygen into blood. Since nitrogen is the major component of air, decreasing the concentration gradient for nitrogen across the microbubble improves left ventricular and myocardial videointensity following intravenous injection. Exposing the microbubbles to a non-toxic gas having a lower blood solubility and/or microbubble diffusivity than that of nitrogen and having a gas density of greater than about 0.300 lb/ft$^3$ during sonication increases the size and stability of the microbubbles in sonicated dextrose albumin, while lowering the solubility and diffusivity of the microbubbles in blood.

The most preferred contrast agent of this invention is a perfluorobutane-enhanced sonicated dextrose albumin solution comprised of a sonicated three-fold dilution of 5% human serum albumin with 5% dextrose. During sonication, said solution is perfused with perfluorobutane for about 80 seconds, which lowers the solubility and diffusivity of the microbubble gas. The resulting microbubbles are concentrated at room temperature for at least about 120±5 minutes, wherein the excess solution settles in the sonicating syringe. The excess solution is expelled and the concentrated microbubbles are transferred to a sterile syringe and injected intravenously into a mammal.

A second method or preparation includes hand agitatin 15±2 ml of sonicated dextrose albumin with 8±2 ml of a perfluorobutane gas prior to sonication. Sonication then proceeds for 80±5 seocnds.

Using perfluorobutane gas to enhance the sonicated contrast agent of this invention will result in a higher degree of myocardial opacification, endocardial border delineation, and enhanced detection of left-sided ultrasound Doppler signals, upon peripheral venous administration. Additionally, using perfluorobutane gas during sonication creates a more stable microbubble concentration, which subsequently enables ultrasonic visualization of the liver and kidneys following an intravenous injection.

The following examples demonstrate the effect of inert gases on microbubble stability and diffusibility, and the superior results of perfluorobutane as compared to other perfluorocarbon gases on myocardial uptake and videointensity as well as on ultrasonic determination of renal perfusion. In all the following examples all parts and percentages are by weight, unless stated otherwise. All dilutions are by volume.

EXAMPLES

Preparation of Contrast Agents

Albumin (human) USP, 5% solution (hereinafter referred to as "albumin") and dextrose USP, 5% solution (hereinafter referred to as "dextrose") were obtained from a commercial source. The sonicating system used for sonication was a Heat System Ultrasonic Processor Model XL2020 (Heat Systems Inc., Farmingdale, N.Y.). The ½ inch horn transducer was a resonating piezoelectric device. The ½ inch sonicating horn tip was sterilized prior to each sonication.

Sonication of Samples

Sixteen milliliter aliquots of albumin diluted 1:3 with dextrose were drawn up into a 35 cc "Monoject" syringe (Becton Dickinson and Company, Rutherford, N.J.) and sonicated for 80±1 seconds. The "Leur-Lok" of the 35 milliliter syringe was then attached to a stopcock. After mixing the dextrose albumin solution by hand for about 7 to about 10 seconds, the plunger was removed from the top of the syringe. The sterile sonicating horn was then lowered into the open end of the syringe until at the surface of the albumin-dextrose solution. The solution was placed at the horn tip and manually held at this position while continuously sonicating at a frequency of 20.000 Hz and a power output of 210 W for 80±1 seconds to form a stable microbubble solution.

Gas Perfusion of Samples

During sonication, the dextrose albumin mixture was exposed to either perfluoropropane or perfluorobutane gas (Commercial Grade, 99.9% by weight). The gas was drawn up into a sterile syringe through a 0.22 µM filter (Micron Separations Inc., Westborough, Mass.) to prevent contamination. During sonication, 5 milliliters of perfluorocarbon gas was manually injected into the solution, over the 80 second time interval, through the stopcock so that the microbubbles produced contain this less soluble gas. The total volume of perfluorocarbon-enhanced sonicated dextrose albumin produced with this formulation was 25±2 milliliters. These samples were then used for intravenous injection.

Microbubble Analysis

Microbubble size and purity was determined using hemocytometry. Microscopic inspection of the microbubbles was performed to determine if any coalescent microbubbles were present in the solution. Microbubble concentration was determined using a Coulter Counter. The contrast agent was rejected for use if any of the following conditions are present: the mean microbubble size was 4.0 to 6.0 microns; coalesced microbubbles or strands were detected by light microscopy; or the mean microbubble concentration was less than $0.8 \times 10^9$ or greater than $1.5 \times 10^9$ microbubble/milliliter. The sample was also rejected if the number of microbubbles greater than 10 microns in the sample was greater than 4%.

All samples were stored in 35 milliliter syringes until time of injection. All solutions were given within 36 hours of production. All samples were prepared in a laminar flow hood.

Preparation of Open-Chest Dogs

Mongrel dogs of either sex (15-30 kilograms) were anesthetized with sodium pentobarbital (30 milligram per kilogram intravenously), intubated, and ventilated initially with room air using a positive pressure respirator. A left thoracotomy was performed under sterile conditions and the pericardium incised. In addition to a 19 gauge peripheral intravenous line, eight French Catheters were placed in the femoral artery and vein for intravenous administration of ultrasound contrast agents and pressure monitoring. Through one femoral venous sheath, a 7F balloon-tipped thermodilution catheter was placed in the pulmonary artery using fluoroscopy for determination of pulmonary artery pressure and cardiac output. A 7F pigtail catheter was introduced into the left ventricle for pressure measurements (left ventricular systolic and end-diastolic pressure) following injection of each ultrasound contrast agent.

Following adequate surgical exposure, a 3.5 Megahertz ultrasound transducer connected to a commercially available ultrasound scanner (Hewlett Packard Company; Andover, Mass.) was placed in a warm water bath. The bath overlays the anterior epicardial surface. The transducer was mounted on a clamp and lowered into the bath. It was adjusted until an optimal stable short axis view of the left and right ventricle had been obtained at the ventricular mid-papillary muscle level. These images could then be used to assess left ventricular cavity and myocardial uptake of contrast following intravenous injection.

Example 1

Safety and Efficacy of Perfluorobutane-Sonicated Dextrose Albumin (DF-SDA) in Dogs Three open chest dogs were used to measure anterior and posterior myocardial peak videointensity produced by either a 0.015 or 0.03 milliliter per kilogram intravenous injection of DF-SDA. These values were compared with the videointensity produced in these same regions by a 0.06 ml/kg intravenous injection of perfluoropropane-enhanced sonicated dextrose albumin (PESDA). Left ventricular and pulmonary artery pressures were measured before and after injection, as well as cardiac output.

The degree of left ventricular cavity shadowing was significantly less with DF-SDA than with PESDA in 5 dogs. This was verified in Table 1, where the peak posterior myocardial videointensity produced with DF-SDA was significantly higher than that produced by PESDA. This was entirely due to the significant decrease of left ventricular shadowing. As can be seen in Table 2, these doses of DF-SDA did not cause any change in pulmonary artery pressures or left ventricular pressures.

TABLE 1

| Peak Myocardial Videointensity of DF-SDA Compared with PESDA in Dogs | | |
|---|---|---|
| Contrast Agent | PVI (Anterior Wall) | PVI (Posterior Wall) |
| DF-SDA | 2.8 ± 0.6 unit | 2.5 ± 0.6 unit |
| PESDA | 2.1 ± 0.4 unit | 0.4 ± 0.3 unit |

TABLE 2

| Effect of DF-SDA on Pressures | | |
|---|---|---|
| | Before Injection | After Injection |
| Mean Pulmonary Artery Pressure | 15.5 ± 2.2 mmHg | 15.6 ± 2.9 mmHg |
| Left Ventricular Systolic Pressure | 93.5 ± 3.0 mmHg | 93.3 ± 5.4 mmHg |
| Left Ventricular End-Diastolic Pressure | 0.3 ± 0.7 mmHg | 0.3 ± 0.7 mmHg |

Example 2

Stability of Perfluorobutane-Sonicated Dextrose Albumin

The stability of DF-SDA over a 48-hour time period was also determined in three separate samples. Measurements of mean microbubble size, percentage of microbubbles above 10 microns, and mean microbubble concentration were performed immediately after production and again at 36 hours after production. Neither microbubble size nor concentration changed over this time period. These data are summarized in Table 3 below.

TABLE 3

| DF-SDA Stability | | |
|---|---|---|
| | Immediate | 48 Hours |
| Mean size | 4.7 ± 2.5µ | 4.8 ± 2.7µ |
| Mean concentration | $1.60 \times 10^9$ | $1.68 \times 10^9$ |
| % Microbubbles >10 microns | 2.5% | 3.6% |

Example 3

Perfluorobutane-Sonicated Dextrose Albumin Effects on Human Blood

Eight blood samples from four human volunteers were obtained to assess the effect of perfluorobutane gas on white and red blood cell counts. Each person had one sample exposed to 2 milliliters of perfluorobutane and one of their samples exposed to room air. As can be seen, there was no effect of perfluorobutane on white or red blood cell count, platelet count, or number of abnormal red blood cells seen on the peripheral blood smear (Table 4). (Results are the average of four volunteers' blood samples.)

TABLE 4

Effect of Perfluorobutane on Blood

| | Before Perfluorobutane | After Perfluorobutane |
|---|---|---|
| White blood count | $6.7 \times 10^3$ | $6.6 \times 10^3$ |
| Red blood count | $4.8 \times 10^6$ | $4.8 \times 10^6$ |
| Platelet count | Adequate | Adequate |

Therefore, perfluorobutane does not appear to adversely affect blood or sonicated albumin.

These preliminary data in animals and in-vitro studies with human blood demonstrate the safety of intravenous DF-SDA. It is critical to study the safety of DF-SDA in patients with coronary artery disease during resting and stress echocardiography. Perfluorobutane has already been used safely in humans during intraocular surgery and we anticipate from this information and our preliminary data that it will be safe in humans.

Example 4

Use of Perfluoropropane and Perfluorobutane Enhanced Sonicated Dextrose Albumin to Determine Myocardial Blood Flow in Humans For humans, doses of from about as small as 0.0025 up to 0.08 ml/kg are given depending on the ultrasonic procedure used. The contrast agent is given by peripheral intravenous injection over 3–5 seconds followed by a 10 milliliter normal saline flush. (The dose range is patient-specific: large patients may require slightly higher doses to produce equivalent left ventricular contrast effects). Generally a patient would receive a 0.01 ml/kg of perfluoropropane sonicated dextrose albuminor 0.0015 ml/kg perfluorobutane sonicated dextrose albumin, as the initial injection. If this fails to produce myocardial opacification, the dose would then be doubled. The dose which produces myocardial opacification and improved detection of abnormal wall motion and left ventricular ejection fraction is used to determine myocardial blood flow by contrast echocardiography performed using the standard technique as described in Weyman, Arthur E., "Principles and Practice of Echocardiography", Lea & Febiger, Malvern, Pa. (1994, 2d Edition) and using the commercially available Hewlett Packard Sonos 1500 Phased Array Imaging System (Hewlett Packard, Andover, Mass.). Throughout the echocardiographic procedure, the patient's heart rate, blood pressure and oxygen saturation are monitored and recorded. The peak videointensity (corrected for baseline intensity) in the left ventricular cavity and myocardium for each injection is obtained.

Myocardial contrast produced from intravenous injection of two different molecular weight perfluorocarbon containing microbubbles in humans. The peak anterior myocardial videointensity (PMVI) and duration of acoustic shadowing (AS) produced by up to 0.02 ml/kg intravenous injection of perfluoropropane (molecular weight 188 grams per mole (g/m)) exposed sonicated dextrose albumin (C3SDA) were compared with 0.007 ml/kg intravenous injection of perfluorobutane exposed sonicated dextrose albumin (C4SDA) in 24 patients.

| PCMB | N | Dose | PMVI | AS (Sec) | % 1 – 2 + MC |
|---|---|---|---|---|---|
| C3SDA | 14 | .02 ± .08 | 2.1 ± 1.5 | 50 ± 15 | 5 (36%) |
| C4SDA | 10 | .007 ± 0.01* | 1.9 ± 1.8 | 31 ± 21* | 8 (80%) |

*$p < 0.05$ compared to C3SDA

Despite lowering the dose, intravenous injection of C4SDA produced significantly higher myocardial contrast, with significantly less AS. Thus intravenous perfluoropropane and perfluorobutane exposed sonicated dextrose albumin can be used safely in humans with significantly better myocardial contrast for perfluorobutane than for lower molecular weight perfluoropropane.

As can be seen from the foregoing, the invention accomplishes at least all of its objectives.

What is claimed is:

1. A pharmaceutically acceptable ultrasound contrast agent which relies on microbubbles for echogenicity, said agent comprising:

microbubbles formed from a solution of a filmogenic protein and a saccharide wherein said saccharide comprises less than about 40% by weight of said solution wherein said microbubbles have an internal atmosphere enhanced with perfluorobutane gas.

2. The contrast agent of claim 1 wherein said filmogenic protein is human serum albumin.

3. The contrast agent of claim 2 wherein said human serum albumin is diluted 2 to 8 fold with dextrose.

4. The contrast agent of claim 3 wherein said human serum albumin is a 5% by weight solution.

5. The method of claim 4 wherein said dextrose is a 5% by weight solution.

6. The contrast agent of claim 1 wherein said saccharide is dextrose.

7. A sonicated aqueous albumin-dextrose ultrasound contrast agent solution comprising:

between about a two-fold and about an eight-fold dilution of aqueous albumin with between about 5% to about 50% by weight aqueous dextrose solution;

said albumin between about 2% to about 10% by weight solution; and microbubbles the gaseous content of which contain an amount of perfluorocarbon gas which is effective for visually detecting myocardial perfusion upon echocardiogram following peripheral intravenous injection of said agent into a host.

8. The contrast agent of claim 7 wherein said dilution of albumin with dextrose is a 3-fold dilution.

9. The contrast agent of claim 8 wherein said human serum albumin is a 5% by weight solution.

10. The contrast agent of claim 8 wherein said dextrose is a 5% by weight solution.

11. A method for myocardial, renal or hepatic opacification comprising the steps of:

(a) obtaining an echo contrast agent solution which comprises:

(i) forming an aqueous albumin-dextrose solution containing between about a two-fold and about an eight-fold dilution of between about 5% to about 50 by weight dextrose and between about 2% to about 10% by weight human serum albumin, and (ii) sonicating said mixture to form microbubbles the gaseous content of which contain an amount of perfluorocarbon gas which is effective for visually detecting myocardial perfusion by echocardiogram following peripheral intravenous injection of said agent into a host;

(b) introducing said echo contrast agent into a host by intravenous injection; and (c) performing an echo contrast study on said host using a suitable Doppler or ultrasound echo apparatus.

12. A pharmaceutically acceptable contrast agent which relies on microbubbles for echogenicity, said agent comprising:

microbubbles with an interior atmosphere enhanced with perfluorobutane gas.

13. A pharmaceutically-acceptable ultrasound contrast agent which relies on microbubbles for echogenicity prepared by the method of:

combining a denaturable protein and a saccharide to form a solution wherein said saccharide comprises less than about 40% by weight of said solution;

perfusing said solution with fluorobutane gas;

sonicating said solution during said perfusion so that microbubbles are formed with an internal atmosphere comprising said perfluorobutane gas.

14. The method of claim 13 wherein said saccharide is dextrose.

15. The method of claim 13 wherein said protein is human serum albumin.

* * * * *